US00PP23011P2

(12) United States Plant Patent
Smith

(10) Patent No.: US PP23,011 P2
(45) Date of Patent: Sep. 4, 2012

(54) ***CHRYSANTHEMUM* PLANT NAMED 'SYAID REDFI'**

(50) Latin Name: *Chrysanthemum×morifolium*
Varietal Denomination: Syaid Redfi

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 27 days.

(21) Appl. No.: 13/065,407

(22) Filed: Mar. 22, 2011

(51) Int. Cl.
*A01H 5/00* (2006.01)

(52) U.S. Cl. ..... Plt./293; Plt./286

(58) Field of Classification Search ..... Plt./286, Plt./293
See application file for complete search history.

*Primary Examiner* — Susan McCormick Ewoldt
(74) *Attorney, Agent, or Firm* — Joshua L. Price

(57) ABSTRACT

A new *Chrysanthemum* plant named 'Syaid Redfi' particularly distinguished by the small greyed-red inflorescences, medium green foliage, compact, rounded and mounded plant habit, with a natural flowering season of early September.

1 Drawing Sheet

Latin name of the genus and species of the plant claimed: *Chrysanthemum×morifolium.*

Varietal denomination: 'Syaid Redfi'.

BACKGROUND OF THE NEW PLANT

The present invention comprises a new *Chrysanthemum*, botanically known as *Chrysanthemum×morifolium*, and hereinafter referred to by the variety name 'Syaid Redfi'.

'Syaid Redfi' is a product of a planned breeding program. The new cultivar has small greyed-red inflorescences, medium green foliage, compact, rounded and mounded plant habit, with a natural flowering season of early September.

'Syaid Redfi' originated from a hybridization made in January 2005 in a controlled breeding environment in Salinas, Calif. The female parent was the unpatented, proprietary plant designated '01-M300' with red colored inflorescences, little smaller plant size and a natural flowering season of about one week later.

The male parent of 'Syaid Redfi' was identified as a unpatented, proprietary plant designated '00-M401' with larger, coral colored inflorescences, with more disc florets, larger plant size and a natural flowering season of about 10 days later. The resultant seed was sown in June 2005 in Alva, Fla.

'Syaid Redfi' was selected as one flowering plant within the progeny of the stated cross in October 2005 in a controlled environment in Alva, Fla.

The first act of asexual reproduction of 'Syaid Redfi' was accomplished when vegetative cuttings were propagated from the initial selection in November 2005 in a controlled environment in Alva, Fla.

BRIEF SUMMARY OF INVENTION

Horticultural examination of plants grown from cuttings of the plant initiated in November 2005, and continuing thereafter, has demonstrated that the combination of characteristics as herein disclosed for 'Syaid Redfi' are firmly fixed and are retained through successive generations of asexual reproduction.

'Syaid Redfi' has not been observed under all possible environmental conditions. The phenotype may vary significantly with variations in environment such as temperature, light intensity and day length.

A Plant Breeder's Right for this cultivar was applied for in Canada on Apr. 9, 2010 (No. 10-6929). 'Syaid Redfi' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Syaid Redfi' with colors being as true as possible with an illustration of this type. The photographic drawing shows a flowering potted plant of the new variety.

DETAILED BOTANICAL DESCRIPTION

The plant used for the photographs was about 10 weeks old grown in Monroeville, N.J. in an outdoor trial. One rooted cuttings grown in a nine inch pot with no terminal pinching of the apices. The photograph was taken in mid September 2010 in New Jersey.

The plant descriptions and measurements were taken in Gilroy, Calif. in May 2010 under natural light. Plants were grown under conditions which approximate those generally used for potted *Chrysanthemum* trials in a greenhouse. These plants used in the descriptions were about 10 weeks old.

Color references are made to The Royal Horticultural Society Colour Chart (R.H.S.) 2001.

TABLE 1

DIFFERENCES BETWEEN THE NEW VARIETY 'SYAID REDFI' AND A SIMILAR VARIETY

| | 'Syaid Redfi' | 'Urano Red/Bronze' (Unpatented) |
|---|---|---|
| Inflorescence color: | More red | More bronze than red |
| Plant habit size: | Larger | Smaller |
| Natural flowering season: | | |
| Lastingness of inflorescence color: | Lasts almost twice as long | Does not last as long |

Plant:

*Form, growth and habit.*—Herbaceous decorative garden-type, stems upright and outwardly spreading, freely branching, strong and moderately vigorous growth habit.

*Plant height.*—11-13 cm.

*Plant height (inflorescence included).*—20-25 cm.

*Plant width.*—33-37 cm.

*Garden performance and tolerance to weather.*—Very good.

*Crop time to flowering.*—About 10 weeks.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—Darker than RHS 137A.

*Lower surface.*—RHS 137B but appears lighter because of hairs.

*Mature, leaf color, upper surface.*—Darker than RHS 137A.

*Lower surface.*—RHS 137B but appears lighter because of hairs.

*Length.*—3.3-3.5 cm.

*Width.*—2.7-2.8 cm.

*Shape.*—Broadly ovate.

*Base shape.*—Attenuate.

*Apex shape.*—Mucronulate.

*Margin.*—Irregularly and palmately lobed; slightly dentate.

*Texture, upper surface.*—Bifid T-shaped hairs.

*Lower surface.*—Bifid T-shaped hairs.

*Color of veins, upper surface.*—RHS 144B.

*Color of veins, lower surface.*—RHS 144B.

*Petiole color.*—RHS 144B.

*Length.*—0.5-0.6 cm.

*Diameter.*—0.25 cm.

*Texture.*—Bifid T-shaped hairs.

Stem:

*Quantity of main branches per plant.*—5 with lots of branching.

*Color of stem.*—Closest to RHS 138A, appears more greyed because of hairs.

*Length of stem.*—10-12 cm.

*Diameter.*—0.4-0.5 cm.

*Length of internodes.*—1.5-2.2 cm.

*Texture.*—Bifid T-shaped hairs.

*Color of peduncle.*—RHS 138A, but appears more greyed because of hairs.

*Length of peduncle.*—6.5-11.0 cm.

*Peduncle diameter.*—0.2 cm.

*Texture.*—Bifid T-shaped hairs.

Inflorescence:

*Type.*—Compositae type, solitary inflorescences, decorative-type, borne terminally above foliage, ray florets arranged acropetally on a capitulum.

*Quantity of short days to flowering (response time).*—About 46 days.

*Quantity of inflorescences per plant.*—100 plus approximately 75 buds.

*Lastingness of individual blooms on the plant.*—About 6 weeks from first inflorescences.

*Fragrance.*—Slightly spicy.

Bud (just when opening/showing color):

*Color.*—RHS 187A.

*Length.*—0.8-1.0 cm.

*Width.*—1.0-1.1 cm.

*Shape.*—Oblate.

Immature inflorescence:

*Diameter.*—3.5-4.0 cm.

*Color of ray florets, upper surface.*—Closest to RHS 183A-RHS 183B but with a little more red.

*Lower surface.*—RHS 9C ground overlaid shades RHS 78C.

Mature inflorescence:

*Diameter.*—4.2-4.5 cm.

*Depth.*—1.5 cm.

*Total diameter of 'disc'.*—0.4-0.45 cm (only found on very mature).

*Receptacle height.*—0.25-0.3 cm.

Receptacle diameter.—0.4 cm.

Ray florets:

*Average quantity of florets.*—Approximately 150 in numerous whorls.

*Color of florets, upper surface.*—Closest to RHS 183B; fades to RHS 179A to RHS 180B.

*Lower surface.*—RHS 179A to RHS 179B mottled.

*Length.*—1.8-2.0 cm.

*Width.*—0.65-0.7 cm at widest.

*Shape.*—Broad spoon.

*Apex shape.*—Praemorse.

*Margin.*—Entire.

*Texture, upper surface.*—Papillose.

*Lower surface.*—Papillose.

Disc florets:

*Average quantity of florets.*—20-25; appear very late.

*Color of florets.*—RHS 155C basally, RHS 9B apex.

*Length.*—0.5 cm.

*Width.*—0.1 cm.

*Shape.*—Tubular, elongated.

*Apex shape.*—Acute, 5 pointed.

Phyllaries:

*Quantity.*—Approximately 30.

*Color, upper surface.*—RHS 138A but appear lighter because of hairs.

*Lower surface.*—RHS 138B.

*Length.*—0.4-0.6 cm.

*Width.*—0.15-0.2 cm.

*Shape.*—Ovate to lanceolate.

*Apex shape.*—Acute.

*Base.*—Fused.

*Margins.*—Entire; Papery.

*Texture, upper surface*.—Glabrous.
*Lower surface*.—Bifid T-shaped hairs.

Reproductive organs:
*Pistil*.—1.
*Length*.—0.6-0.7 cm.
*Style color*.—RHS 1C.
*Style length*.—0.3 cm.
*Stigma color*.—RHS 9C.
*Stigma shape*.—Bi-parted.
*Ovary color*.—Not observed.
*Stamens*.—1.
*Color of filaments*.—RHS 1C.
*Length filaments*.—0.2 cm.
*Anther color*.—RHS 3B.
*Anther length*.—0.1 cm.
*Anther shape*.—Oblong.
*Color of pollen*.—Not observed.
*Pollen amount*.—Not observed.
*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'Syaid Redfi' substantially as illustrated and described herein.

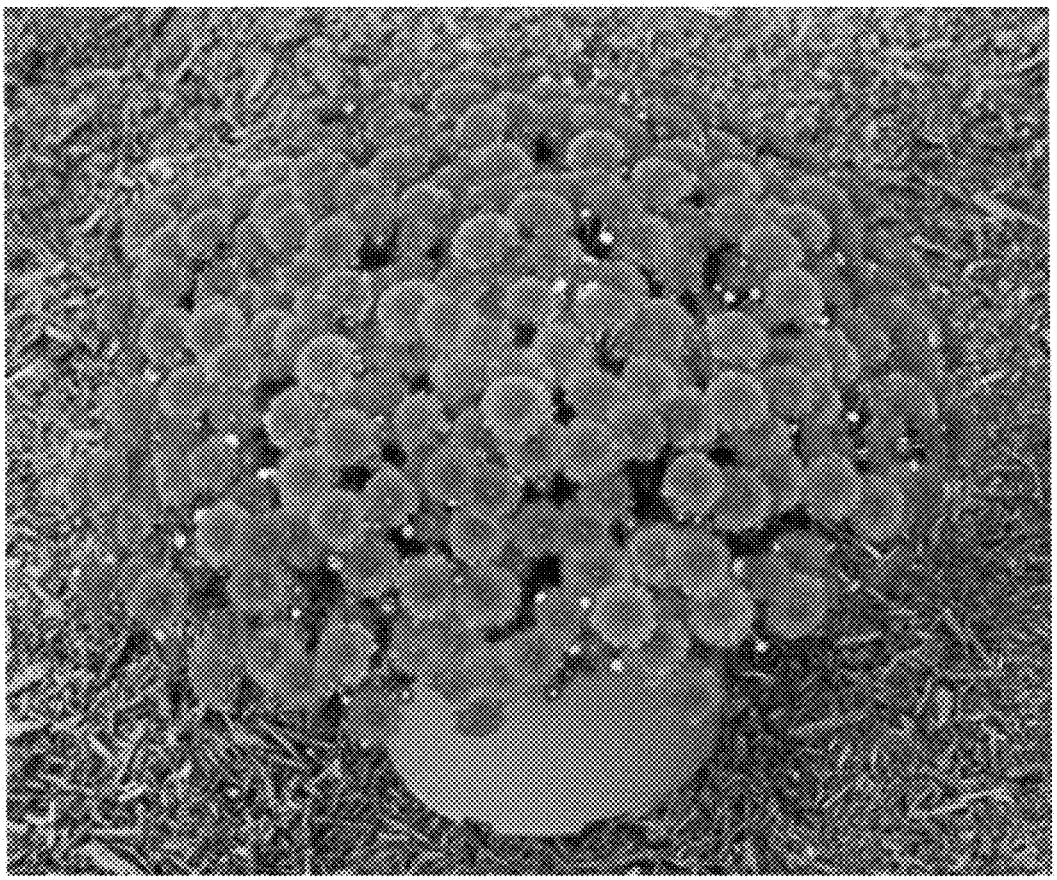

* * * * *